United States Patent [19]

Gennari

[11] Patent Number: 4,621,056

[45] Date of Patent: Nov. 4, 1986

[54] PROCESS FOR PRODUCING STABLE SULPHO-ADENOSYL-L-METHIONINE SALTS

[75] Inventor: Federico Gennari, Truccazzano, Italy

[73] Assignee: Bioresearch S.p.A, Milan, Italy

[21] Appl. No.: 637,051

[22] Filed: Aug. 2, 1984

[30] Foreign Application Priority Data

Aug. 24, 1983 [IT] Italy ................ 22622 A/83

[51] Int. Cl.$^4$ .............. C12P 19/28; C07H 19/06
[52] U.S. Cl. ............................ 435/85; 536/26
[58] Field of Search ..................... 435/85; 536/26

[56] References Cited

U.S. PATENT DOCUMENTS

| | | | |
|---|---|---|---|
| 3,893,999 | 7/1975 | Fiecchi | 536/26 |
| 3,954,726 | 5/1976 | Fiecchi | 536/26 |
| 4,057,686 | 11/1977 | Fiecchi | 536/26 |
| 4,109,079 | 8/1978 | Kawahara et al. | 536/26 |
| 4,242,505 | 12/1980 | Kawahara et al. | 536/26 |
| 4,465,672 | 8/1984 | Gennari | 536/26 |
| 4,543,408 | 9/1985 | Gennari | 536/26 |

FOREIGN PATENT DOCUMENTS

| | | | |
|---|---|---|---|
| 2275220 | 1/1976 | France | 536/26 |
| 076486 | 7/1974 | Japan | 536/26 |
| 0107485 | 9/1978 | Japan | 536/26 |
| 0099499 | 8/1981 | Japan | 536/26 |
| 2116172 | 9/1983 | United Kingdom | 435/85 |

*Primary Examiner*—Jerome D. Goldberg
*Assistant Examiner*—Joseph A. Lipovsky
*Attorney, Agent, or Firm*—Stevens, Davis, Miller & Mosher

[57] ABSTRACT

A process is described for the large-scale industrial production of any stable SAMe salt at very high purity and with a yield of about 90% or more.

The new process is characterized by the following basic operations: (a) production of yeast containing 12-20 g/kg of SAMe, (b) cell lysis and recovery of the SAMe-rich lysate, (c) ultrafiltration of the lysate, (d) passage through weak acid ion exchange resin, (e) passage through absorption resin, (f) concentration by reverse osmosis, (g) spray-drying the concentrated aqueous solution of SAMe salt.

3 Claims, No Drawings

PROCESS FOR PRODUCING STABLE SULPHO-ADENOSYL-L-METHIONINE SALTS

This invention relates to a new process for the large-scale industrial production of stable sulpho-adenosyl-L-methionine (SAMe) salts from yeasts highly enriched in SAMe.

Sulpho-adenosyl-L-methionine (I) is known to be the main biological donor of methyl groups.

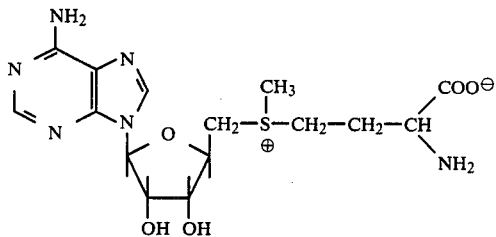

This special characteristic has made it a subject of considerable interest, firstly from the biochemical aspect and subsequently because of its possible therapeutic applications.

The main problems connected with the large-scale use of this molecule are its thermal instability, even at ambient temperature, and the complexity of its preparation and purification.

It has therefore been the subject of wide research and numerous patents by the present applicant, directed to obtaining stable salts and processes for the preparation of such salts which can be implemented on an industrial scale. Patents of the applicant relating both to stable SAMe salts and their preparation methods include: U.S. Pat. Nos. 3,893,999; 3,954,726; 4,057,686: European patent application No. 82107333.5.

The processes described in the aforesaid patents are specific for determined salts or groups of salts. Furthermore, although they give excellent results when used on a limited scale, they become onerous when used for producing very large quantities of SAMe salts.

In this respect, the processes described up to the present time comprise one or more of the following operations:
- precipitating the SAMe contained in yeast lysates enriched with SAMe (5–7 g/kg of SAMe) with picrolonic acid, and then eliminating the picrolonic anion
- passing the SAMe through a column of weak acid ion exchange resin
- purifying the SAMe salt by treatment with activated carbon or by passage through a column of activated carbon
- concentration under vacuum at 30°–35° C.
- lyophilisation of the final salt, all of which are operations which if carried out on relatively small quantities of product do not present special difficulties or unacceptable costs, whereas they become practically impossible when applied to high product production levels, both because of the energy costs and because of the volumes involved.

A new process has now been found, and forms the subject matter of the present invention, for the production of stable SAMe salts which can be equally used economically and simply for the large-scale production of any SAMe salt, with very pure product yields which have never been previously attained. The new process according to the present invention essentially comprises the following stages:

(a) SAMe enrichment of the yeast which contains it, by adding methionine in successive stages until a final SAMe concentration of 12–20 g/kg of moist yeast is attained;

(b) cell lysis and recovery of the aqueous SAMe-rich solution (lysate);

(c) treating the lysate by ultrafiltration with a U.F. membrane of 10,000 M.W. nominal cut-off;

(d) passing the lysate, after U.F. prepurification, through a column of weak acid ion exchange resin having a particle size of between 100 and 200 mesh;

(e) passing the eluate of the preceding column through an absorption resin column;

(f) concentrating the eluate of the preceding column by reverse osmosis using a high rejection reverse osmosis desalination membrane;

(g) drying the concentrated aqueous solution by means of a spraydryer.

The enrichment stage (a) can be carried out on any suitable yeast (for example Saccharomyces cerevisiae, Torulopsis utilis, Candida utilis and the like) by the known Schlenk enrichment method (Enzymologia, 29, 238 (1965)) by the addition of methionine.

The applicant has however found that it is critical for the implementation of the process according to the present invention to repeat the enrichment operation several times until a final SAMe ion concentration of between 12 and 20 g/kg of moist yeast is attained.

All processes described up to the present time have used an enriched starting yeast containing 6–7 g/kg of SAMe. Higher enrichment has been neither considered nor thought advantageous in the industrial production of SAMe salts.

Stage (b) is carried out by treating the yeast enriched with SAMe up to 12–20 g/kg firstly with water and ethyl acetate, and then with sulphuric acid of between 0.1 N and 0.5N, and preferably 0.35N, at ambient temperature, so as to cause cell lysis and to cause practically 100% of the SAMe present to pass into solution.

Preferably, water and acetate quantities of between 1/20 and 1/5 of the weight of the moist cells are used, and treatment is continued for a time of between 15 and 45 minutes, and preferably 30 minutes.

Sulphuric acid is then added, and the lysis is continued for a time of between 1 and 2 hours, and preferably 1½ hours.

It should be noted that the described lysis method is not the only known method, but is the preferred method in that it is carried out at ambient temperature under such conditions that the solution can be easily filtered from the cell residues.

The ultrafiltration stage (c) is not essential for the purposes of the present process, but is preferably carried out when the lysate contains protein residues. In this respect, it has been found that such protein residues adhere to the resin used in the next stage, so progressively reducing its activity.

The ultrafiltration must be carried out using membranes having a nominal cut-off of 10,000 M.W., and either flat or tubular, but preferably tubular.

It has been found that when the lysate is subjected to ultrafiltration under these conditions, the resin columns used in the next stage have a considerably greater average life, to the decisive benefit of production costs. The lysata purified by ultrafiltration is fed in stage (d) to a column of weak acid resin (COOH) of particle size between 100 and 200 mesh, in H+ form at a pH of between 3.5 and 7, and preferably 5, at a rate of between 1 and 3 volumes of liquid/hour per volume of resin, and preferably 2.

As stated, the passage of SAMe solutions through weak acid ion exchange resin columns for purification purposes is a known operation. It has however been surprisingly found that if using a resin of the said characteristics but with a particle size of between 100 and 200 mesh (in comparison with the greater 50 mesh particle size of normally used columns) an eluate is obtained which contains very pure SAMe, and in particular free from organic salts, polypeptides and degradation products. The only residual impurities with the treatment according to the present invention are 5'-deoxy-5'-methylthioadenosine (3-10%) accompanied by small quantities of adenine and traces of coloured compounds.

The quantity of resin used is 10-50 l per kg of SAMe, and preferably 30.

The lysate is passed through the column, washed with a quantity of distilled water, and then with 0.1M acetic acid until the eluate has a pH of less than 3, and again with a quantity of distilled water, after which the SAMe is eluted with 0.2N $H_2SO_4$.

If a salt other than the sulphate is required, it is eluted with a 0.2N solution of the required acid.

The quantity and quality of the residual impurities after this treatment means that traatment of the SAMe with activated carbon after elution is superfluous, this treatment being considered essential in the known art.

This is another of the extremely advantageous aspects of the new process, because the activated carbon, although being effective, retains a SAMe quantity at least equal to 15% of its own weight, thus leading to a considerable yield reduction.

In contrast, it has been unexpectedly found that the impurities contained in the SAMe after passage through the weak acid resin of 100-200 mesh particle size are totally removed by passage through a simple absorption polymer. Suitable polymers are Amberlite XAD2, XAD4, and XAD7, which practically retain no SAMe from a strongly acid solution such as the eluate from stage (d).

Stage (e) is carried out by passing the eluate through a column of the aforesaid resin at a rate of between 0.2 and 1 volume of liquid/hour per volume of resin, and preferably 0.5.

The quantity of resin used is 10-50 liters per kg of SAMe, and preferably 30. The SAMe solution is passed through the column and then washed with 20 mN $H_2SO_4$ (or other required acid) until the SAMe disappears from the eluate.

The eluate containing about 10g/l of very pure SAMe is fed to the next stage for concentration.

The concentration stage (f) employing reverse osmosis is carried out by subjecting the eluate from stage (e) to a reverse osmosis process using high NaCl rejection reverse osmosis desalination membranes, which are able to practically completely retain the SAMe, whereas the water and the excess part of the sulphuric acid or other equivalent acid are eliminated in the permeate.

Polyamide membranes are preferably used because of their good resistance in a strongly acid solution.

Concentration by reverse osmosis enables the eluate from stage (e) to be concentrated from 10 g/l to 100-200 g/l and preferably 120 g/l.

It should be noted that the use of reverse osmosis for concentrating the SAMe solutions compared with other previously known methods (for example concentration under vacuum) has two great advantages:
(1) concentration is effected at a maximum temperature of 20° C. compared with the 30°-35° C. necessary for concentration under vacuum. This is very important in view of the thermal instability of SAMe
(2) if the eluate contains an excess of $H_2SO_4$ over the stoichiometric of the final salt, this acid is eliminated during reverse osmosis, thus obviating the use of Ba hydroxide for its precipitation, with the consequent difficulties of filtering the $BaSO_4$ and the relative incraased costs.

The use of this concentration method, which as stated is extremely advantageous in the new process according to the invention, has been made possible by the particular degree of concentration and purity with which the SAMe leaves the preceding stages, and the method could in no way have been used in processes of the known art.

The solution of SAMe concentrated by reverse osmosis is analysed for its concentration of SAMe and sulphuric acid (or other acid if another salt is required), and suitable additions of sulphuric acid and/or other acids are made in order to obtain the required stoichiometric composition.

For example, the stoichiometric composition is adjusted to obtain a solution of SAMe disulphate-p-toluenesulphonate.

This solution is then fed to the next stage (g) involving spraydrying in order to obtain the final product.

In stage (g) the product is atomised in a drying chamber fed with hot air.

The concentration of the inlet solution (expressed as SAMe ion) is between 100 and 200 g/l and preferably 120 g/l.

The feed temperature of the drying air, preferably previously dehumidified, is between 140° and 200° C., and preferably 160° C. The temperature of the outlet air is between 40° and 100° C., and preferably 60° C.

Under these conditions, the product which leaves has a temperature of between 40° and 50° C. and is rapidly cooled to ambient temperature by dehumidified air. The plant should be provided with a suitable device for continuously extracting the dry product.

All the aforesaid conditions are critical in preventing the SAMe salt undergoing drying from attaining a temperature at which it could decompose.

It should be noted that spray-drying SAMe salts has never been previously possible because of the sensitivity of the salts to high temperature.

The feasibility of such a new process stage unexpectedly arises as a consequence of the degree of concentration at which the product leaves the new reverse osmosis stage, and as a consequence of having determined the critical inlet and outlet air temperature, dehumidification and extraction rate conditions which allow the products to be dried without undergoing any degradation.

It should also be noted that spray-drying the SAMe salts in accordance with the present invention leads to large cost reductions in terms of equipment and energy, compared with known drying methods, and in particular drying by lyophilisation.

In conclusion, the new process for producing SAMe salts on an industrial scale according to the present invention, which is new in each of its stages and new overall, allows very pure product to be obtained at yields never attained heretofore, namely close to 90% or more, by means of a process which is much simpler and less costly than all previously known processes.

This truly surprising result has been obtained as a consequence of having unexpectedly found a certain number of critical parameters which govern the new process.

In order to make the process according to the present invention more easily reproducible and to illustrate some of the resultant advantages obtained, some practical examples are given hereinafter for purely illustrative purposes, but which in no case limit the scope of the protection and claims.

EXAMPLE 1

Preparation of SAMe disulphate-p-toluenesulphonate 110 liters of ethyl acetate and 110 liters of water are added at ambient temperature to 720 kg of yeast enriched with SAMe (17 g/kg) by the Schlenk method (Enzymologia 29, 283 (1965)).

After energetic agitation for 30 minutes, 1000 liters of 0.35N sulphuric acid are added, and agitation continued for a further 1½ hours.

The mixture is filtered through a rotary filter, and the cake washed with water to obtain 2800 l of solution containing 4.40 g/l of SAMe, equivalent to 99.5% of that present in the starting material.

The SAMe solution thus obtained (pH 2.5) is fed to an ultrafiltration plant with tubular membranes of 10,000 cut-off.

The permeate leaving the membranes is collected in a suitable container, while the concentrate is continuously recycled until it attains a final volume of 200 l. At this point, distilled water is added, and recycling continued until theSAMe is completely extracted.

3500 l of ultrafiltered lysate are obtained, which are adjusted to pH 5 by adding 2N NaOH.

A column is prepared containing 400 l of AMBERLITE CG 50 in H+ form, carefully washed with distilled water.

The lysate is passed through the resin column at a rate of 800 l/h, which is kept constant during the entire process.

400 l of distilled water, 3200 l of 0.1M acetic acid and 400 l of distilled water are then passed successively.

The SAMe is eluted with 800 l of 0.2N sulphuric acid. The 800 l of eluate obtained in this manner contain about 11.6 kg of SAMe.

A column is prepared containing 400 l of AMBERLITE XAD4 resin previously activated with 800 l of 0.1 N NaOH and 800 l of 0.1 N $H_2SO_4$ and then carefully washed with distilled water.

The previously obtained SAMe solution is passed through the column at a rate of 200 l/h, which is kept constant during the entire process.

400 l of 20 mN sulphuric acid are then passed through.

The eluate containing the SAMe (about 1000 l containing 11.3 kg of SAMe) is collected.

The solution thus obtained is fed to a reverse osmosis plant of the flat type containing polyamide desalination membranes.

In this plant the SAMe solution is concentrated to 80 l containing 11.2 kg of SAMe.

1.8 kg of concentrated $H_2SO_4$ and 4.8 kg of p-toluenesulphonic acid are added.

The solution thus obtained is fed to a spray-dryer fed with air at 160° C.

The dried product is extracted continuously from the spray-dryer.

2.16 kg of powder are obtained, which on analysis shows the following composition:
SAMe: 51%
$H_2SO_4$: 25%
p.toluenesulphonic acid: 22%
$H_2O$: 2%
corresponding to the SAMe.$2H_2SO_4$.p.toluenesulphonic salt. Yield about 90%.

EXAMPLE 2

Preparation of SAMe disulphate-di-p-toluenesulphonate.

The procedure of Example 1 is followed until and including concentration by reverse osmosis.

1.8 kg of concentrated $H_2SO_4$ and 9.6 kg of p-toluenesulphonic acid are added to the concentrated solution from the reverse osmosis.

Drying is carried out as in Example 1.

26.5 kg of powder are obtained, which on analysis shows the following composition:
SAMe: 41.5%
$H_2SO_4$: 20.5%
p.toluenesulphonic acid 36%
$H_2O$: 2%
corresponding to the SAMe.$2H_2SO_4$.2 p.toluenesulphonic salt. Yield about 90%.

EXAMPLE 3

Preparation of SAMe. 2.5sulphate

The procedure of Example 1 is followed until and including concentration by reverse osmosis.

3.5 kg of concentrated $H_2SO_4$ are added to the concentrated solution from the reverse osmosis.

Drying is carried out as in Example 1.

18.2 kg of powder are obtained, which on analysis shows the following composition:
SAMe: 60.6%
$H_2SO_4$: 37.4%
$H_2O$: 2%
corresponding to the salt SAMe. 2.5 $H_2SO_4$. Yield about 90%.

I claim:

1. A process for producing stable salts of SAMe from yeast concentrates which contain it, comprising:
   (a) adjusting the SAMe concentration in the starting yeast to 12–20 g/kg of moist yeast;
   (b) preparing a lysate of high SAMe concentration from the enriched yeast obtained from step (a) by treating the same with water and ethyl acetate quantities of between 1/20 and 1/5 of weight of the moist cell for a time of between 15 and 45 minutes and subsequently with $H_2SO_4$ at a concentration between 0.1 N and 0.5 N;
   (c) subjecting the lysate obtained from step (b) to ultrafiltration carried out with membrane of 10,000 M.W. nominal cut-off to obtain a filtered liquid;
   (d) passing the filtered liquid maintained at pH between 3.5 and 7, through a weak acid ion-exchange resin of —COOH type, in the H+ form, said resin having particle size between 100 and 200 mesh, and subsequently eluting SAMe with aqueous solution 0.2 N of a strong acid;

(e) passing the eluate obtained from step (d) through an absorption polymer selected from the group consisting of polystyrene and acrylic esters, at a rate of between 0.2 and 1 volume of liquid/hour per volume of resin;

(f) subjecting the eluate obtained from step (e) to reverse osmosis with high NaCl rejection reverse osmosis desalination membranes, until a SAMe content of 100–200 g/l is obtained in the concentrate, and subsequently treating the concentrated SAMe solution with a stoichiometric quantity of acid in order to transform it totally into the required SAMe salt; and (g) drying the concentrated solution of SAMe salt in a spray-dryer, wherein the air has inlet temperature between 140° and 200° C. and outlet temperature between 40° and 100° C.

2. A process according to claim 1, further comprising that the adjusting to step (a) is carried out by treating the yeast with methionine stepwise in successive stages.

3. A process according to claim 1, further comprising that the step of passing the filtered liquid through the resin of step (d) is carried out at a rate of between 1 and 3 volumes of liquid/hour per volume of resin.

* * * * *